US008279445B2

(12) United States Patent
Dominguez Horna et al.

(10) Patent No.: US 8,279,445 B2
(45) Date of Patent: Oct. 2, 2012

(54) INTERFEROMETER AND SENSOR BASED ON BIMODAL OPTICAL WAVEGUIDES, AND DETECTION METHOD

(75) Inventors: Carlos Dominguez Horna, Barcelona (ES); Kirill Zinoviev, Barcelona (ES); Laura Maria Lechuga Gomez, Madrid (ES)

(73) Assignee: Consejo Superior de Investigaciones Cientificas, Madrid (ES)

( * ) Notice: Subject to any disclaimer, the term of this patent is extended or adjusted under 35 U.S.C. 154(b) by 183 days.

(21) Appl. No.: 12/669,307

(22) PCT Filed: Jul. 18, 2008

(86) PCT No.: PCT/ES2008/070142
§ 371 (c)(1),
(2), (4) Date: Jun. 15, 2010

(87) PCT Pub. No.: WO2009/010624
PCT Pub. Date: Jan. 22, 2009

(65) Prior Publication Data
US 2010/0271634 A1 Oct. 28, 2010

(30) Foreign Application Priority Data
Jul. 19, 2007 (EP) .................................... 07381053

(51) Int. Cl.
*G01B 9/02* (2006.01)
(52) U.S. Cl. ....................................................... 356/477
(58) Field of Classification Search .................. None
See application file for complete search history.

(56) References Cited

U.S. PATENT DOCUMENTS

| 6,646,747 | B2* | 11/2003 | Deliwala ........................ 356/477 |
| 2002/0015155 | A1* | 2/2002 | Pechstedt et al. .............. 356/477 |
| 2008/0043248 | A1 | 2/2008 | Ozcan |

FOREIGN PATENT DOCUMENTS

| JP | 2004-145246 | 5/2004 |
| KR | 100726206 | 6/2007 |
| WO | 00/26642 | 5/2000 |

OTHER PUBLICATIONS

International Search Report dated Dec. 19, 2008 from corresponding International Application No. PCT/ES2008/070142.
G. Coppola, et. al, "Temperature Optical Sensor Based on all Silicon Bimodal Waveguide", Proceedings of SESENS 2001, pp. 777-782, Nov. 30, 2001.

* cited by examiner

*Primary Examiner* — Tu Nguyen
(74) *Attorney, Agent, or Firm* — Katten Muchin Rosenman LLP

(57) ABSTRACT

A planar optical waveguide interferometer includes a substrate, a bimodal waveguide having at least one layer deposited on the substrate, and a sensor plate located in a selected area of the upper side of the bimodal waveguide. The bimodal waveguide supports a zero-order and a first-order transverse propagating modes where the transverse propagating modes has different dispersion. The bimodal waveguide is designed for confining light in lateral direction and thus is designed for supporting one lateral mode. The sensor plate is designed for receiving a chemical, biological or physical stimulus. The stimulus changes the effective refractive index of said bimodal waveguide. Chip, sensor and sensing method utilize a planar optical waveguide interferometer are provided.

24 Claims, 9 Drawing Sheets

INTERFEROMETER AND SENSOR BASED ON BIMODAL OPTICAL WAVEGUIDES, AND DETECTION METHOD

FIELD OF THE INVENTION

The present invention relates to interferometers and sensors based on optical waveguides, and more particularly, to interferometers and sensors based on bimodal optical waveguides.

STATE OF THE ART

Detection of a molecule, e.g. protein, glucose or binding between the molecules is a common issue. The amount of reagent or the concentration of the molecules in the solution may be low and highly sensitive devices are required for the detection of the molecules. The detection can be conducted using various methods and techniques. There exists a variety of nanomechanical and optical devices, such as Mach-Zhender interferometers, Surface Plasmon Resonance, Young interferometers, Fabry-Perot interferometers and slab interferometers. Mach-Zhender and Young interferometers are compact devices based on optical waveguides which were introduced long time ago and have been well studied. Today these techniques are considered to be among the most sensitive ones in the field of biomolecular detection, because the simplicity of robust planar structures gives an advantage of relatively simple immobilization procedures. The developed methods and protocols allow for binding the molecules without labeling. This makes experiments less laborious and more repeatable since labeling was a source of error since it interfered with the actual results. Interferometers have normally two branches, one of which, when the interferometer acts as a sensing device, it is provided with a sensor plate, the other one being a reference. Reagent flowing through the sensor plate interacts with the molecules previously immobilized over the waveguide in the window. This changes the refractive index of the cladding layer of the waveguide and subsequently the velocity of light propagation along this waveguide. As a consequence, there is a phase shift between the light waves propagating in the two branches. Mixing these waves produces different results, depending on the type of interferometer: an interference pattern in the case of the Young interferometer and variation of output channel signal in the case of Mach-Zhender interferometer.

However, interferometers with two branches have the drawback of having difficulties in accurate splitting the light. If not well fabricated, the critical symmetry of the Y junction leaves the interferometer prone to reduced modulation depth and losses in sensitivity.

Furthermore, high sensitivity may only be obtained on relatively thin waveguides. Sensitivity is defined by the depth of penetration of the evanescent field of the waveguide into the analyte conjugate to the waveguide, that is to say, into the analyte which is in contact with the waveguide. Penetration depth significantly increases if the waveguide thickness is reduced. This involves difficulties in light coupling due to the mismatch between the intensity distribution of the waveguide propagating mode of thin waveguides and the intensity distribution of a conventional light source.

Initial phase shift adjustment between the interfering light waves in the two branches requires additional technological and engineering efforts.

The aforementioned problems can be partially solved by using bimodal waveguide interferometers. An example of a device working with interference of two propagating modes was presented in Japanese patent application JP2004145246. This device consists of a single-mode waveguide followed by a bimodal waveguide, in turn followed by another single-mode waveguide.

The working principle of the structure described in JP2004145246 is based on interference of two propagating modes in a plane type bimodal waveguide. FIG. 5 shows such a waveguide. Although the physical structure is three-dimensional, from the properties point of view the structure is two-dimensional: In longitudinal direction (referred to in FIG. 5 as X axis), which is the direction of light propagation, the structure has a step or rib 500 which defines a change in thickness along the longitudinal axis. In transverse direction (referred to in FIG. 5 as Y axis), the properties (i.e. refractive index) of the waveguide materials change. In lateral direction (referred to in FIG. 5 as Z axis), the waveguide structure is uniform, because its properties do not change along this lateral direction. The structure is therefore a two-dimensional one (from the propagation point of view, it has a longitudinal dimension and another transverse one).

However, the dimensionality of the device of JP2004145246 prevents the manufacture of long and narrow interferometers capable of detecting ultra small changes in the refractive index of the cladding layer.

Another example of a device working with interference of propagating modes is presented by G. Coppola et al. in "Temperature Optical Sensor Based on all Silicon Bimodal Waveguide", where the lateral modes are involved in generating the interference pattern. This device can be fabricated using a conventional photolithography.

Nevertheless, precise control of the interferometer geometry in lateral direction is strongly required for accurate implementation of the device. This control of the lateral geometry of the device is complex using conventional microelectronics technologies.

In fact, the architecture of the devices in JP2004145246 and G. Coppola et al. implies sequential waveguide structure, which is designed for exciting the modes and for reading the interference signal. This causes some limitations on the sensitivity of the devices and on versatility of their.

SUMMARY OF THE INVENTION

The present invention exploits bimodal waveguide structures where different relative phase retardation between the two propagating modes accumulates when it is subjected to a structural change. The present invention relates also to an optical waveguide interferometer comprising a bimodal waveguide whose propagating modes dispersion is mode order sensitive.

One aspect of the invention relates to a planar optical waveguide interferometer which comprises a substrate; a bimodal waveguide comprising at least one layer deposited on the substrate, the bimodal waveguide being designed for supporting a zero-order and a first-order transverse propagating modes, the transverse propagating modes having different dispersion; a sensor plate located in a selected area of the upper side of the bimodal waveguide, the sensor plate being configured for receiving a chemical, biological or physical input stimulus, that stimulus being capable of changing the effective refractive index of the bimodal waveguide. The bimodal waveguide comprises confining means designed for confining light in lateral direction, the bimodal waveguide being thus designed for supporting one lateral mode.

The interferometer preferably comprises an electromagnetic radiation source configured for leading optical light into the bimodal waveguide. This source is more preferably a laser.

Optionally, the source is integrated within the structure of the substrate.

In a particular embodiment, the interferometer comprises polarizing means.

Optionally, the interferometer comprises focusing means. In a particular embodiment, the focusing means is a lens. In this situation, the central axis of the lens is configured to be misaligned in the transverse direction with respect to the longitudinal symmetry axis of the bimodal waveguide, thereby a first and a second transverse propagating modes being excited within the bimodal waveguide when light from a source is directly focused through said lens towards the bimodal waveguide.

In a particular embodiment, the interferometer comprises an input waveguide connected at one end of the bimodal waveguide, this input waveguide being designed for supporting a single mode in transverse and lateral directions; and an output waveguide connected at the other end of the bimodal waveguide, this output waveguide being designed for supporting a single mode in transverse and lateral directions. The thickness of each of the input and output waveguides is less than that of the bimodal waveguide, such that due to the non-symmetrical geometry of the structure at the junction of the input waveguide and the bimodal waveguide, the single mode is split into first and second transverse propagating modes. Optionally, the interferometer comprises means for coupling electromagnetic radiation into the bimodal waveguide, this means being selected from: end-fire, direct focusing, prism coupling and diffraction grating coupling. The amount of light coupled into the output waveguide depends on the intensity distribution at the junction between the bimodal waveguide and the output waveguide.

In another embodiment, the interferometer comprises coupling means configured for coupling to the bimodal waveguide and to the first and second order modes of light with different incidence angles. Optionally, the coupling means is a diffraction grating coupled to an input of the bimodal waveguide.

Preferably, the bimodal waveguide comprises at least two layers. In this case, each of the layers has different refractive indexes. The refractive index of the second layer is lower than that of the second one.

The effective refractive indexes of the zero-order mode and that of the first-order mode are substantially different. This different dispersion of the transverse propagating modes depends on the propagation velocity on the parameters of the waveguide.

Optionally, the interferometer comprises detection means for measuring at the output of the waveguide changes in the radiation intensity due to the input stimulus. In a particular embodiment, the detection means is a two-section photodetector.

Another aspect of the invention refers to a chip comprising at least one planar optical waveguide interferometer like the aforementioned one.

Another aspect of the invention refers to a sensor comprising a planar optical waveguide interferometer like the aforementioned one.

Finally, the present invention relates to a sensing method comprising the following steps: (a) defining a sensor plate in a determined area of a bimodal waveguide of an optical waveguide interferometer; (b) placing a chemical, biological or physical stimulus in the sensor plate; (c) introducing or causing changes in the stimulus; (d) coupling a zero-order mode and a first-order mode of electromagnetic radiation into the bimodal waveguide, in such a way that when both modes travel through the sensor plate defined in the bimodal waveguide, they suffer a phase delay which is dependent on the changes in the stimulus; (d) coupling the first and second order modes of electromagnetic radiation into the bimodal waveguide, such that when both modes traverse the plate defined in the bimodal waveguide, a phase delay which is dependent on the changes in the stimulus occurs; (e) at the output of the bimodal waveguide, measuring the response of the zero-order mode relative to the response of the first-order mode; and (f) relating the relative responses of both modes to the changes caused in the stimulus.

Preferably, the step of measuring the response of the zero-order mode relative to that of the first-order mode comprises: generating a pattern of interference fringes; and measuring a displacement of the interference pattern. Furthermore, the step of relating the relative responses of both modes to the changes in the stimulus comprises relating the displacement of the interference pattern with the presence of changes in the determined stimulus.

The advantages of the proposed invention will become apparent in the description that follows.

BRIEF DESCRIPTION OF THE DRAWINGS

To complete the description and in order to provide for a better understanding of the invention, a set of drawings is provided. Said drawings form an integral part of the description and illustrate a preferred embodiment of the invention, which should not be interpreted as restricting the scope of the invention, but just as an example of how the invention can be embodied. The drawings comprise the following figures:

FIG. 2b shows an implementation of the example of FIG. 2a.

DESCRIPTION OF THE PREFERRED EMBODIMENTS OF THE INVENTION

Figure 6:
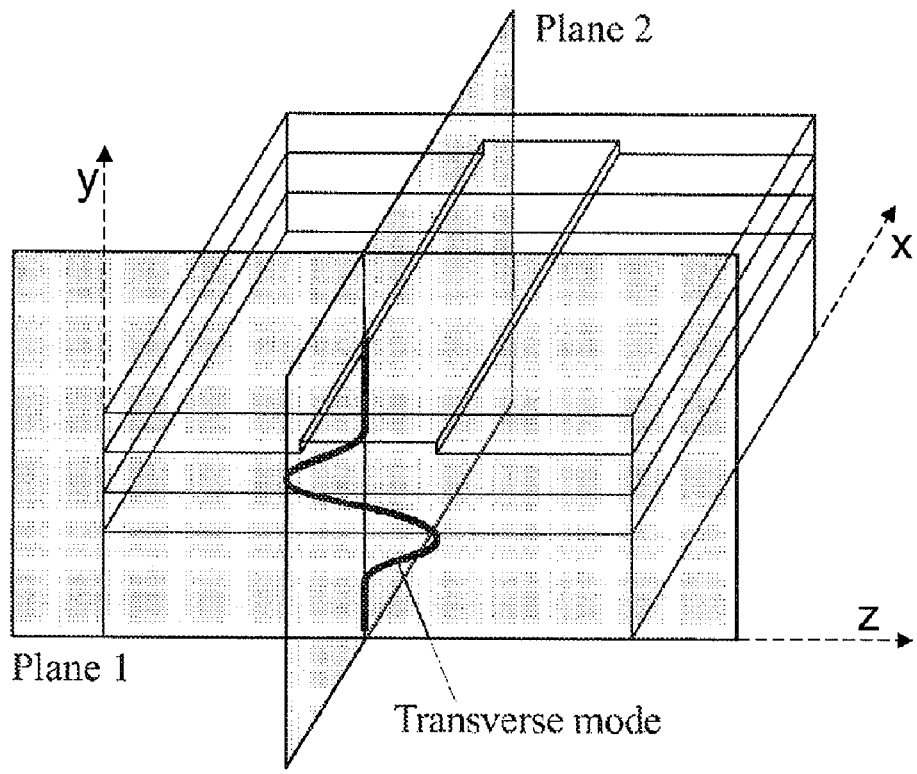
FIGS. 6 and 7 illustrate a waveguide wherein the meaning of "transverse" and "lateral" according to the present invention is explained.

In the context of the present invention, the following drawings must be considered:

As illustrated in FIG. 6, a "transverse mode" of a light beam of electromagnetic radiation is a determined intensity pattern of radiation measured along a line formed by a plane (plane 1 or plane YOZ) perpendicular to the propagation direction of light beam and a plane (plane 2 or plane XOY) perpendicular to a waveguide structure and going along the propagation direction. In the context of the present invention, the term "vertical" is to be considered as a synonym of "transverse".

Figure 7:
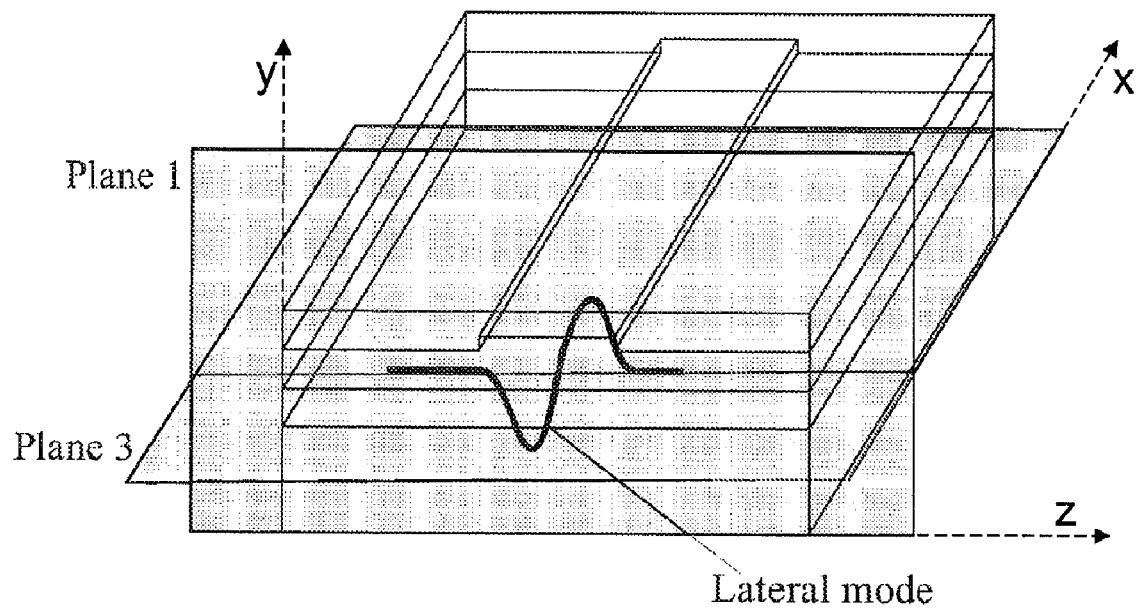

As illustrated in FIG. 7, a "lateral mode" of a light beam of electromagnetic radiation is a determined intensity pattern of radiation measured along a line formed by a plane (plane 1 or plane YOZ) perpendicular to the propagation direction of light beam and to a plane (plane 3 or plane XOZ), also perpendicular to the waveguide structure, and going along the propagation direction. In the context of the present invention, the term "horizontal" is to be considered as a synonym of "lateral".

The transverse and lateral modes can be classified into TE (transverse electric) modes and TM (transverse magnetic) modes. TE modes are those which have no electric field in the propagation direction, while TM modes are those which have no magnetic field in the propagation direction.

The "dispersion" of a waveguide mode is a dependence of the propagation velocity of said mode on the parameters of the waveguide and its surrounding layers.

"Analyte" is any solution containing a substance which is to be detected by the interferometer and sensor of the present invention.

Figure 1A:
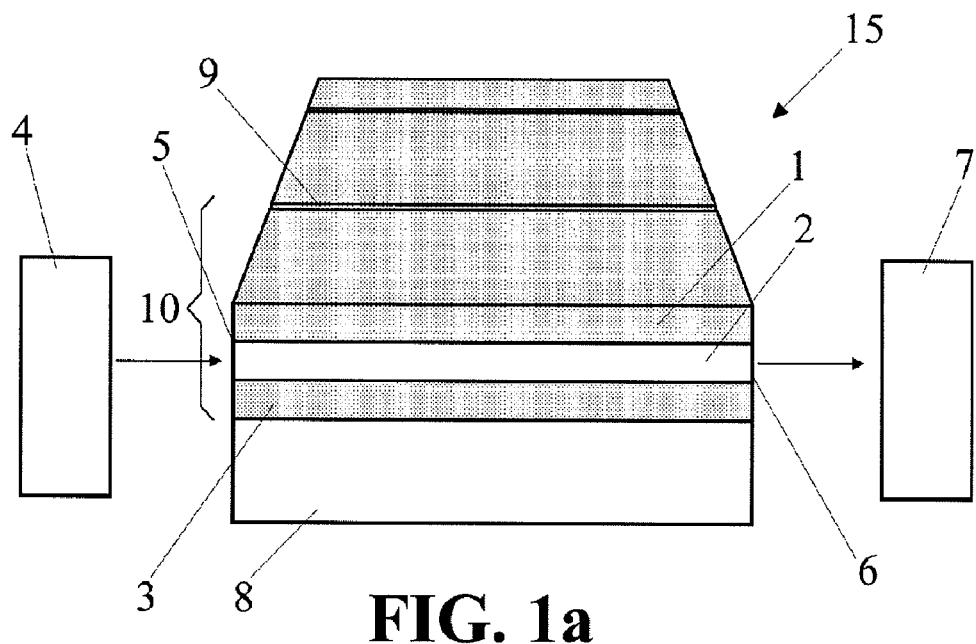
FIGS. 1a to 1c are schematic representations of optical waveguide interferometers according to the present invention.

The implementation of the present invention can be carried out as follows:

FIG. 1a shows a schematic representation of a single optical waveguide 10 which supports two modes of the present invention. The two modes the waveguide 10 is capable of supporting are transverse modes (TE or TM): a fundamental TE or TM mode and a first order TE or TM mode. Although two lateral modes could be chosen, in order to overcome the already mentioned disadvantages derived from structures confining two lateral modes, a structure confining two transverse modes is chosen and designed.

This optical waveguide 10 acts as an interferometer. The optical waveguide 10 comprises at least one layer 2 of optically transparent material deposited in a laminar fashion onto a substrate 8. Preferably, the waveguide 10 comprises several layers 1 2 3 of optically transparent material deposited in a laminar fashion onto a substrate 8. Layer 2 is of higher refractive index than that of adjacent layers 1 and 3. Therefore, in this case the optical waveguide 10 is an optical slab waveguide. The waveguide can have a single layer: One layer 1 over the substrate is enough, because, as will be explained later, an analyte deposited over the upper layer (which can be the only layer) also forms a layer (a covering layer) located above the waveguide 10. Thus, the working principle of the interferometer according to which light travels through a structure with areas having different refractive index is fulfilled, said two areas being the monolayer waveguide 10 (supported on the substrate 8) and the analyte or covering layer deposited thereon. Preferably, a plurality of layers 1 2 3 are used in order to optimize the structure.

The waveguide 10 comprises confining means capable of confining light in lateral direction. Thanks to this confining means 9, the waveguide can support at least one lateral mode.

It is remarked that, in an ideal situation with a perfect waveguide, wherein confinement in transverse direction is provided, a light beam with relatively wide lateral distribution (about 1 mm, for example) would propagate substantially without divergence. This means that after propagating transversally for several millimeters, the light beam would maintain the same width for about 1 mm. In this case no rib or ridge would be required. However, wide light beams make the waveguide bulky and impractical in the sense of integration of many waveguides in an array on one and the same chip. In the narrow light beams (having width of less than about 100 μm) propagating through these waveguides, these end up being very divergent, i.e., after transversally propagating for several millimeters, the light beam diverges and expands several millimeters in lateral direction. This makes the device impractical. In other words, in practice, a single mode operation in lateral direction is extremely difficult when a simple, planar structure is used. Likewise, the longer the waveguide is, the more difficult it is to maintain a single mode operation in lateral direction. For this reason, confining means such as ribs, guides, etc. are necessary.

Single mode operation in lateral direction also facilitates the modeling of the interferometer when working as a sensor and makes predictable its behavior.

Non-limiting examples of confining means 9 are a rib, a ridge or a gradient. Appropriate waveguides are therefore: rib, ridge, gradient or other waveguide structures. Waveguide 10 therefore allows propagation of incident electromagnetic radiation in the direction represented by the length of the waveguide 10, i.e., in the direction represented by the arrow which comes out of the optical source 4. The waveguide 10 is preferably a rectangular waveguide, so that the modes are laterally and transversally confined. The fact that the waveguide is rectangular does not mean that in the plane perpendicular to the propagation direction the waveguide has necessarily rectangular profile. On the contrary, the waveguide cross section may have a small step, forming a rib waveguide structure.

Figure 1B:
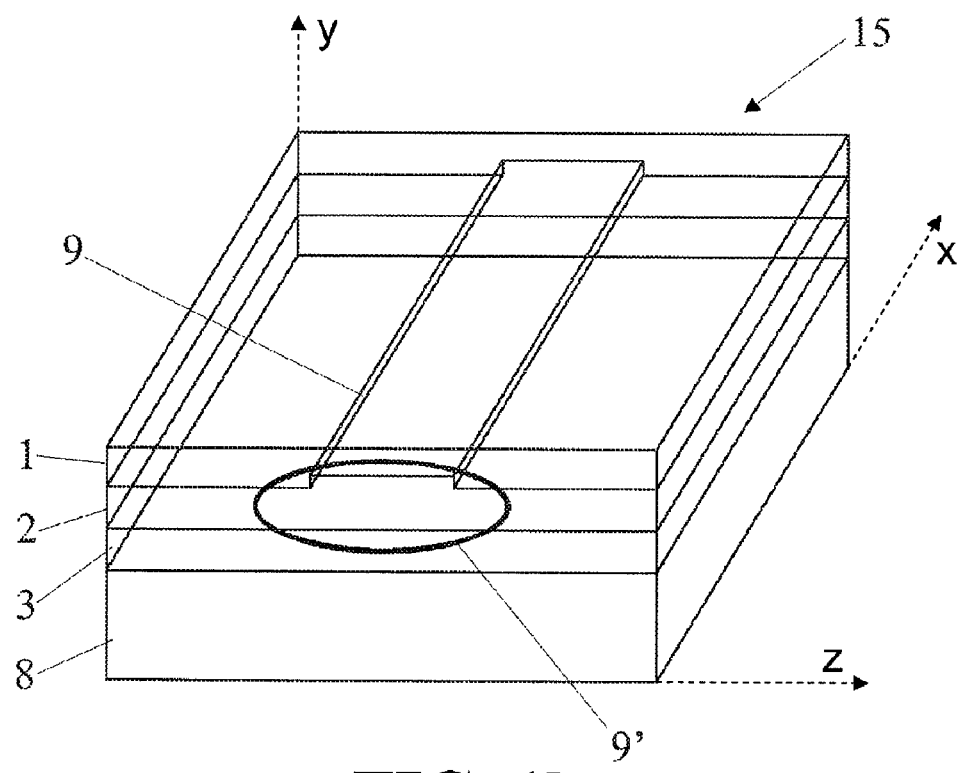
Figure 1C:
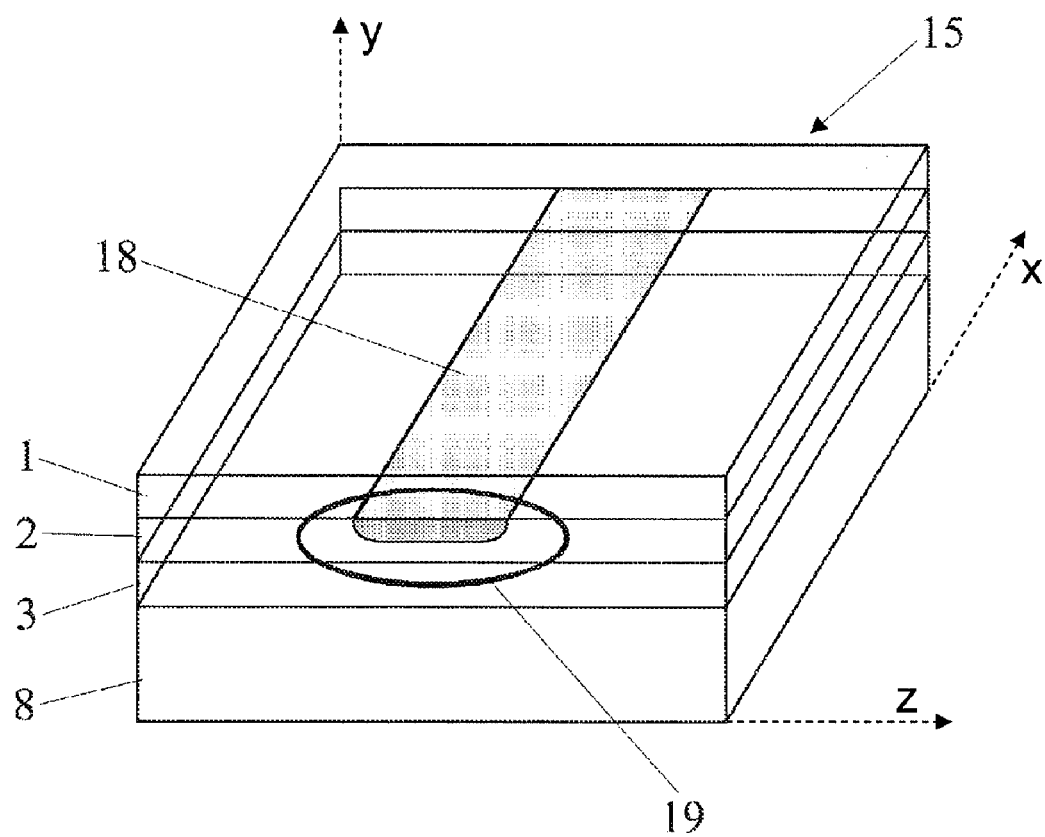

In a particular embodiment, waveguide 10 is a rib type waveguide. This is illustrated in FIG. 1a, wherein the waveguide comprises a rib 9 in the lateral direction (according to the scheme of FIG. 5). This rib 9 implies that the thickness of the waveguide 10 varies along said lateral direction. FIG. 1b shows another view of the same waveguide 10 having a rib 9. Reference 19 in FIG. 1c represents another type of waveguide 10. In FIG. 1b, the three propagation directions are illustrated: longitudinal, X, direction (which is the direction of light propagation), transverse direction, Y, and lateral direction, Z.

As can be seen, the structure of the present invention is homogeneous in relation to the direction of light propagation, while the structure disclosed in JP2004145246 is homogeneous or uniform in lateral direction.

Figure 3:
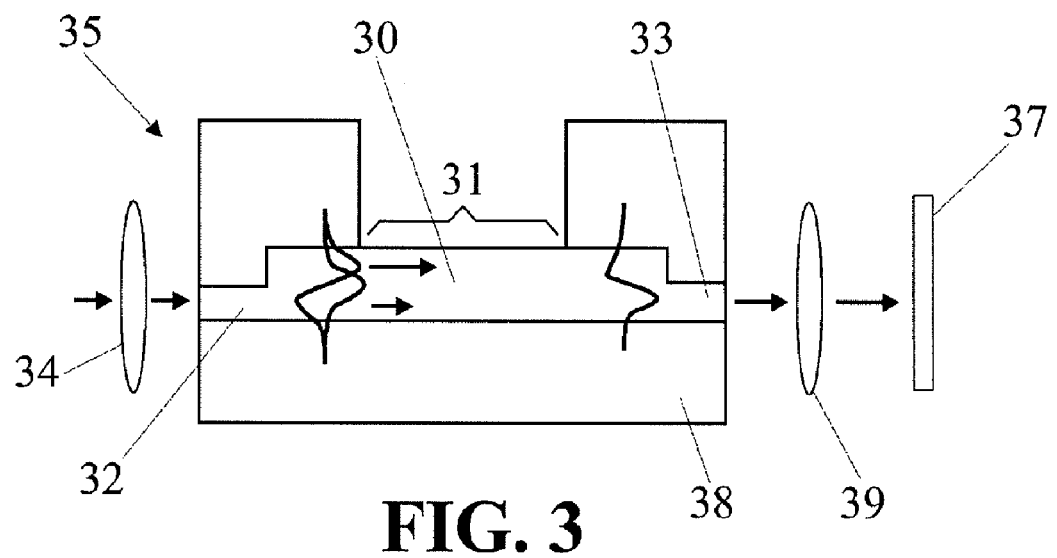
FIG. 3 illustrates an example of an interferometer and sensor according to the present invention.
Figure 4:
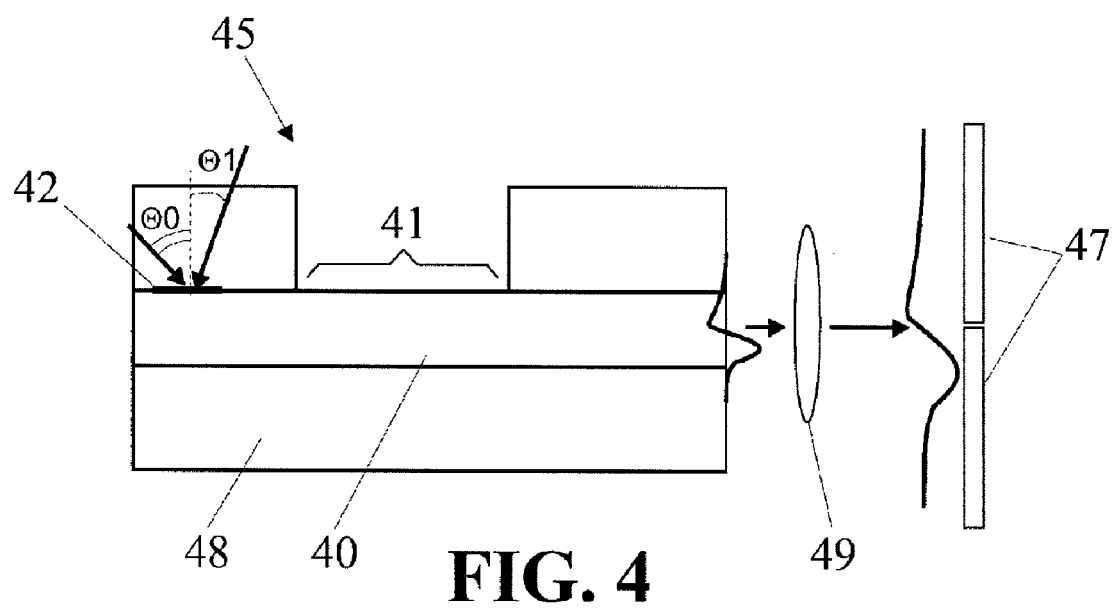
FIG. 4 illustrates an example of an interferometer and sensor according to the present invention.

Although not illustrated in FIGS. 1a-1c, the structure also comprises a sensor plate or area which is formed over a surface of the waveguide using a standard photolithography and wet etching. This sensor plate is illustrated in FIGS. 2 to 4.

One of the advantages of this 2D structure is that the waveguide confines single mode light (thus is able to propagate light) for several centimeters without light divergence in lateral direction. Single mode operation in lateral direction is required because of the following reasons: First, when the waveguide is used as an interferometer or as a sensor, it helps to avoid ambiguities in the control of the interference pattern created at the waveguide end. Second, narrow waveguides, which can only be implemented by two-dimensional structures (i.e. ribs, ridges, etc.) allow sequencing the sensor area to a fraction of square millimeter. The sensor area can vary from about 0.05 to about 1 mm². As a matter of example, a 15 mm long and 0.01 mm wide waveguide has an area of 0.15 mm².

Sensitivity is very important in the device of the present invention. The structure needs to be long enough in order to work as a waveguide interferometer, because its sensitivity is proportional to the length of the sensor plate or area or to the length of the bimodal waveguide. Thus, the length of the structure is preferably in a range approximately between 0.5 and 5 cm.

FIG. 1c shows how the waveguide 10 formed by an installed waveguide may be designed by installation. Reference 18 represents an area wherein waveguide 19 is implanted. The refractive index changes in this area 18. Said waveguide suffers a spatial change with respect to the refractive index in transverse and lateral directions, while geometrically it keeps being a plane slab structure.

Light from a source 4 may be transmitted to the input end of the waveguide 10 so as to illuminate layer 2. Preferably, the light source 4 provides light having a wavelength falling within the visible or near infrared range, said range is approximately between 400 and 1600 nm. Light source 4 is preferably a laser.

The two transverse propagating modes are thus equally excited and travel through the length of the waveguide 10, accumulating different phase delay. At the output end 6 of the waveguide 10, light can radiate from the end surface onto a screen or measuring device 7. The intensity distribution represents the accumulated relative phase delay. Non-limiting examples of measuring devices are detectors, such as one or more photodiodes. If more than one photodetector is used, they are arranged in an array, such as a two-dimensional photodiode array or a CCD camera.

The elements already described and illustrated in FIG. 1a form a planar optical waveguide interferometer 15.

The two transverse modes are capable of exhibiting a measurable relative response to a change in the wavelength of incident electromagnetic radiation or in a localized environment. If the refractive index of layer 1 locally changes, a different relative phase delay accumulates and the intensity distribution is modified accordingly. Optical waveguide transverse modes have an electric field that is distributed among the layers 1 2 3 and in some cases through the substrate 8 of the waveguide structure 10. The relative amount of power contained in the layers 1 2 3 determines the "effective refractive index" of the waveguide mode. In turn, the effective refractive index of a mode determines the propagation speed of that mode and therefore the extent of phase delay that can be accumulated as the mode travels through the waveguide 10. If the refractive index of a layer 1 2 3 changes, the field distribution also changes, thereby resulting in a change in the effective refractive index. If the dispersion properties of the modes are different, then the change in effective refractive index can be quite large. The propagation constants for the fundamental and the first order modes depend on the refractive index of the upper or covering layer. As already mentioned, when the optical waveguide works as an interferometer, and an analyte is deposited over the upper layer 1, the analyte works as a covering layer. In other words, it is necessary that the dispersion (i.e., the dependence of the propagation constants on the refractive index) is different for each mode. The interference pattern of both modes at the end of the waveguide is dependent on the refractive index of the combined layers, and therefore on the analyte solution refractive index.

Figure 1D:
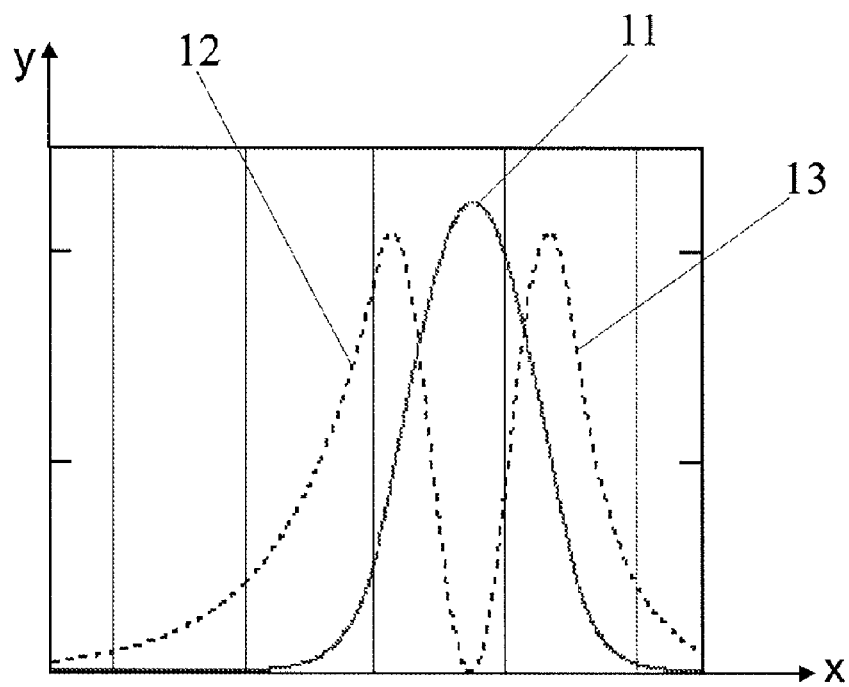
FIG. 1d represents an example of the intensity distribution of the propagating modes in the transverse direction in an optical waveguide interferometer according to the present invention.

FIG. 1d represents an example of the intensity distribution of the propagating modes in the transverse direction. The distance in transverse direction is indicated in X axis in nm. The normalized intensity of the electric field is indicated in the Y axis (the magnitude not being so important as the response or shape). In FIG. 1d, reference 11 represents a distribution of intensity of the fundamental mode. References 12 and 13 represent the distribution of intensity of the first order mode. As can be seen in FIG. 1d, the dispersion effect is due to the markedly different power distribution of both modes.

The optical waveguide structure 10 forming an optical interferometer may be advantageously manufactured using any suitable combination of conventional materials. Examples of conventional manufacture methods are those based on Chemical Vapor Deposition (CVD), such as Plasma Enhancement Chemical Vapor Deposition (PECVD) or Low Pressure Chemical Vapor Deposition (LPCVD).

Chemical Vapor Deposition (CVD) is a chemical process used to produce high-purity, high-performance solid materials, such as thin films. In a typical CVD process, the wafer (substrate) is exposed to one or more volatile precursors, which react and/or decompose on the substrate surface to produce the desired deposit. Microfabrication processes widely use CVD to deposit materials in various forms, including: monocrystalline, polycrystalline, amorphous and epitaxial forms. These materials include: silicon, carbon fiber, filaments, carbon nanotubes, $SiO_2$, silicon-germanium, tungsten, silicon carbide, silicon nitride, silicon oxynitride, titanium nitride, and various high-k dielectrics.

For example, the refractive index of a silicon oxynitride optical waveguide of constant thickness (typically in a range between 0.3 and 0.5 microns) could be selected at any level in the range between 1.457 and 2.00.

Preferably, the first and second waveguide mode can exhibit a measurable relative response to a change in a localized environment caused by the introduction of changes in a determined physical, biological and/or chemical stimulus. This response is caused by the evanescent field of the modes as they extend into the localized environment. An example of introduction of a change in a stimulus is a change in the refractive index of the material (e.g., analyte) placed in that environment. As a consequence of that change, the first and second waveguide modes accumulate different relative phase delay, thereby causing a measurable relative response.

This means that the planar optical waveguide interferometer 15 can advantageously be used to detect the presence of changes in a physical, biological and/or chemical stimulus of an analyte introduced into the localized environment. The optical waveguide interferometer thus becomes a chemical sensor waveguide interferometer or a sensor based on optical waveguide. Non-limiting examples of interaction of the stimulus with the waveguide modes are: binding interaction, absorbance interaction or any other interaction. For example, a gaseous or liquid phase analyte comprising a chemical stimulus may be introduced into the localized environment of the optical waveguide interferometer. Alternatively, a chemical reaction may take place in said environment, causing changes in the nature of the chemical stimulus in situ, thereby causing a change in said environment.

The localized environment, also called sensor layer or plate, is preferably an area or surface of the upper layer 1 of the optical waveguide 10 (not illustrated in FIGS. 1a-1c). This sensor layer may comprise absorbent or bioactive materials. Non-limiting examples of absorbent materials are polymer materials, such as polysiloxane or imprinted polymers. An absorbent material can absorb gases, liquids or vapors comprising a specific chemical stimulus. Non-limiting examples of bioactive materials are those comprising monoclonal and polyclonal antibodies, enzymes, DNA fragments, RNA, aptamers, PNAs, functional proteins or whole cells. A bioactive material may be appropriate for being detected in liquid or gas phase.

An interference pattern is generated inside the bimodal waveguide 10 (acting as an interferometer) when electromagnetic radiation propagates along the waveguide 10. The already mentioned changes in a stimulus located in a localized environment or sensor plate, or a change in wavelength, can be calculated from the relative phase shift of the interference pattern. The measurable response to said change is represented by a displacement of the fringes in the interference pattern. The relative phase shift of the radiation within the interferometer can be calculated by measuring said displacement in the fringes. At the output 6 of the waveguide 10, the electromagnetic radiation is coupled into free space. The interference pattern can thus be recorded in a conventional manner (for example, using a single detector 7 which measures the changes in the radiation intensity or using a plurality of such detectors 7 which monitor the changes occurring in a number of fringes or in the entire interference pattern). Such detectors 7 are preferably one or more photodetectors and upon using more than one photodetector, they are arranged in an array, as a two-dimensional photodiode array.

As shown in FIG. 1a, light from the source 4 is focused in the input end 5 of the waveguide 10 and propagated in the form of electromagnetic radiation, which can be coupled into the first and second waveguide modes in different ways.

In a particular embodiment, radiation is simply coupled to the waveguide 10 by means of the end of a face 5 of said waveguide 10. This is also called "end fire type procedure". In this case, the light source (e.g., laser) is integrated with the laminate structure 1 2 3 on the common substrate 8. Non-limiting examples of substrates 8 are indium phosphate and silicon substrates.

Alternatively, the interferometer 15 comprises other coupling means for coupling the incident electromagnetic radiation into the first (fundamental) and second (first-order) waveguide modes of the waveguide 10. This coupling of both modes is done substantially simultaneously. Non-limiting examples of coupling means, apart from end-fire, are direct focusing (for example, by means of a HeNe laser), prism coupling, diffraction grating coupling or mirror coupling.

Optionally, the incident light or electromagnetic radiation may be oriented (e.g., linearly polarized) as desired using appropriate polarizing means. Non-limiting examples of polarizing means are polarizing cube beam splitters, linear polarizers and wire-grid polarizers.

Optionally, the incident light or electromagnetic radiation may be focused using focusing means. Non-limiting examples of such means are: a lens, a microlens and an optical system comprising a series of lenses.

Optionally, the output electromagnetic radiation pattern may be projected towards the aforementioned detector by means of projecting means. Non-limiting examples of projecting means are objective lenses, lenses and direct projection onto multisection photodetector.

Next, some examples of interferometers based on bimodal waveguides and sensors based on interferometers are described.

Figure 5:
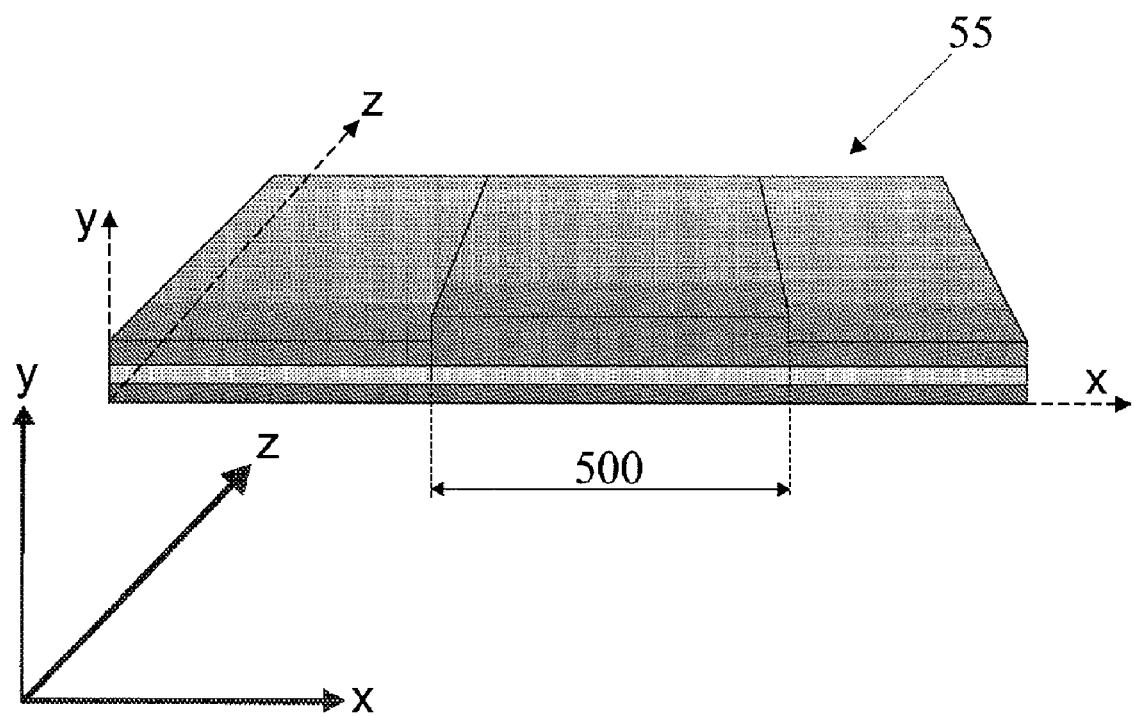
FIG. 5 shows a prior art two-dimensional planar waveguide.

FIG. 2 shows an example of interferometer 25 which comprises a bimodal waveguide 20, formed by one or more layers as illustrated in FIGS. 1a, 1b and 1c. On its upper surface, the waveguide 20 comprises a sensor plate 21, wherein an analyte can be deposited. Waveguide modes (the fundamental and the first order ones) are excited in the waveguide 20 using direct focusing of light from a laser source (not shown in FIG. 2) by means of an objective lens 22. A structure is considered non-symmetrical in transverse direction if the distribution of the refractive index across the structure in transverse direction is not symmetrical with respect to the symmetry axis of the structure. The symmetry axis of the structure is an axis going in the direction of light propagation and crossing the plane perpendicular to the light propagation direction in a point where maximum intensity of electromagnetic field distribution of a transverse fundamental mode is located. The structure of FIG. 5 is thus non-symmetrical. Because the structure is not symmetrical the central axis of the objective lens can be misaligned in the transverse direction with respect to the symmetry axis of the waveguide layer, both the zero (fundamental) and the first order modes are excited. The two transverse modes propagate with different velocities and pass by the sensor plate 21. The interference pattern formed at the output end 16 of the waveguide 20 is projected on a two-section photodetector (TSP) 27 using an objective lens 29 as a projecting and magnifying means. The position of the maximum of the interference pattern is defined, among other parameters, such as the refractive index, the thickness of each layer, the length of the waveguide and the width of the waveguide, by the initial phase of the excited waves and by the refractive index of the analyte passing through the sensor plate 21. It is thus registered the change in the refractive index of the covering layer (measured in the sensor plate) caused by a chemical or biological reaction which has occurred on the waveguide surface or by changes in the analyte solution.

Blocks 28 refer to the walls of a microfluidic cell which can be attached to the waveguide 20 in order to provide flow and exchange of the analyte. They are not part of the present invention.

Figure 2A:
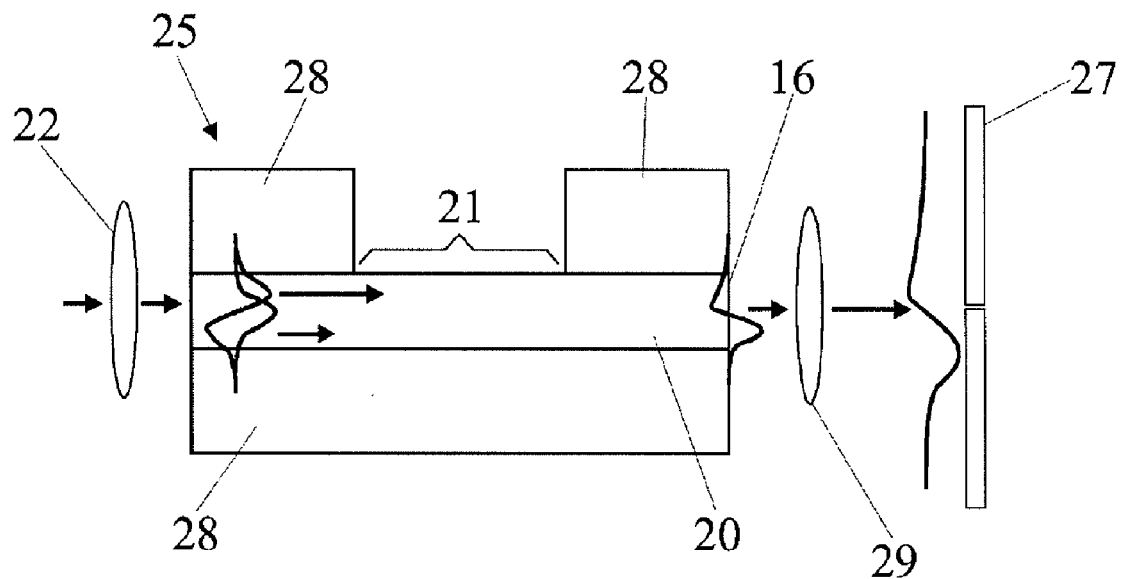
FIG. 2a illustrates an example of an interferometer and sensor according to the present invention.
Figure 2B:
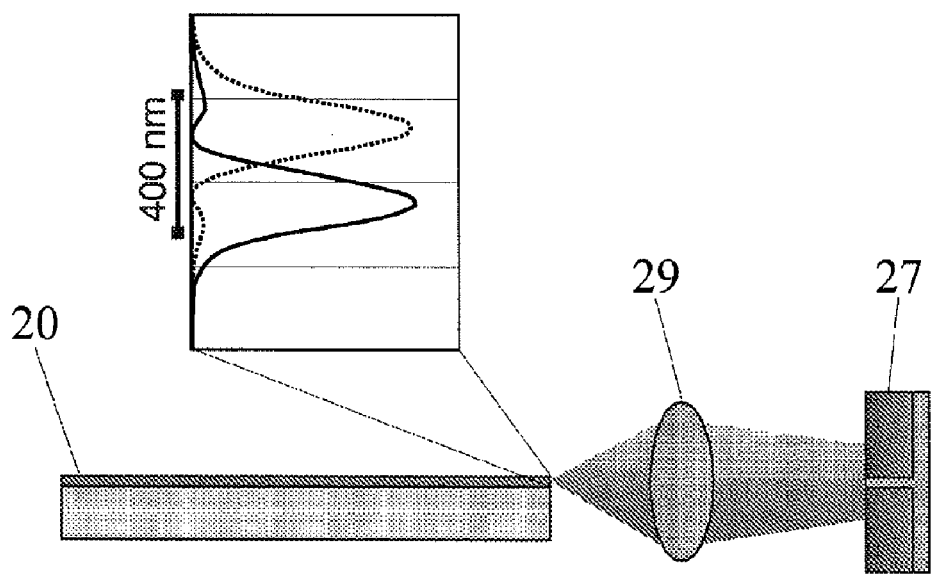

FIG. 2b shows an implementation of the example of FIG. 2a. The interference pattern in the transverse direction can be distributed with the maximum located in the lower or in the upper part of the waveguide, as shown in FIG. 2b, where the distributions of light intensities in the waveguide cross section are shown in the inset. The distributions are designed for a waveguide with refractive index of 2.0 (silicon nitride) and with thickness of 400 nm. The phase difference between the modes varies by u radian from one curve to the other. Under certain conditions the difference between the energies concentrated in the top and in the bottom sections of the photodetector can reach −17 dB. The output intensity is proportional to the amount of light coupled to the waveguide at the input. If absorption over the waveguide is constant, then the total light power at the exit is proportional to the power coupled at the input except for some changes due to reflectivity from the output facet, which according to simulations is slightly changing with the interference pattern movement. Assuming that the function of the reflectivity change is known, the ambiguities due to coupling efficiency variations can be reduced, because monitoring with a two-section photodetector (TSP) allows registering simultaneously both the total power and the shift in the distribution of light exciting the bimodal waveguide (BiMW).

FIG. 3 illustrates an example of interferometer 35 which comprises a bimodal waveguide 30, formed by one or more layers as illustrated in FIGS. 1a, 1b and 1c. On its upper surface, the bimodal waveguide 30 comprises a sensor plate 31 wherein an analyte can be deposited. The interferometer 35 comprises, at both ends of said waveguide 30, single mode waveguides 31 32. Both input waveguide 31 and output waveguide 32 are single mode in transverse and lateral directions. The only parameter which varies from the single mode part 31 32 to the bimodal part 30 is the thickness. This implies that the thickness of these two waveguides 31 32 is less than the thickness of the bimodal waveguide 30. Light is coupled into the input waveguide 32 by any conventional coupling means, such as end-fire, direct focusing, prism coupling or diffraction grating coupling. The particular coupling means used in the interferometer 35 of FIG. 3 is direct coupling by means of a focused lens 34. Because the structure is not symmetrical at the junction input waveguide 32—bimodal waveguide 30, the fundamental mode (which is the only mode which propagates through the input waveguide 32) splits into two modes: the fundamental and the first order ones, in the bimodal waveguide 30. The ratio between the modes amplitudes is defined by the geometry of the structure or, more precisely, by the thickness of the waveguides 32 30 31. Optimization of the wavelength thickness is an engineering problem which can be solved on the basis of conventional modeling methods. The amount of light coupled into the output waveguide 33 depends on the intensity distribution at the junction bimodal waveguide 30—output waveguide 33. In this example, the reading of the output signal coming out of the output waveguide 33 is performed by a conventional photodetector 37, such as a photodiode. The output interference pattern is projected on said photodetector 37 using an objective lens 39 as a projecting means.

FIG. 4 illustrates an example of interferometer 45 which comprises a bimodal waveguide 40 deposited on a substrate 48. On its upper surface, the bimodal waveguide 40 comprises a sensor plate 41 wherein an analyte can be deposited. Light is coupled into the bimodal waveguide 40 by means of a diffraction grating coupler 42 mounted or integrated on the bimodal waveguide 40. The fundamental and the first order modes are excited by light beams (e.g., laser) coming from a single source (not illustrated in FIG. 4) and directed to the diffraction grating coupler 42 at different incidence angles $\theta_0$ $\theta_1$ corresponding to the phase match condition for each mode. Both modes are diffracted by diffraction grating coupler 42 and propagate through the bimodal waveguide.

As already mentioned, sensitivity is directly proportional to the length of the sensor plate or to the length of the bimodal waveguide. Next, an analysis of the sensitivity of the device of FIG. 2b is done.

If the transfer matrix approach is used, the distributions of light intensities are created for each mode of a waveguide with a refractive index 2.0 (silicon nitride) on a silica substrate (refractive index 1.46) and a variable refractive index of the cladding layer. Then, the distributions of the interference pattern at the waveguide exit and the corresponding signals generated by the photodetector sections are calculated as a function of the phase shift between the modes. The signals produced by the photodetector sections are recalculated into a relative change, $S_r$, of the output signal according to the expression:

$$S_r = \frac{U_{up} - U_{down}}{U_{up} + U_{down}}, \quad (1)$$

Figure 8:
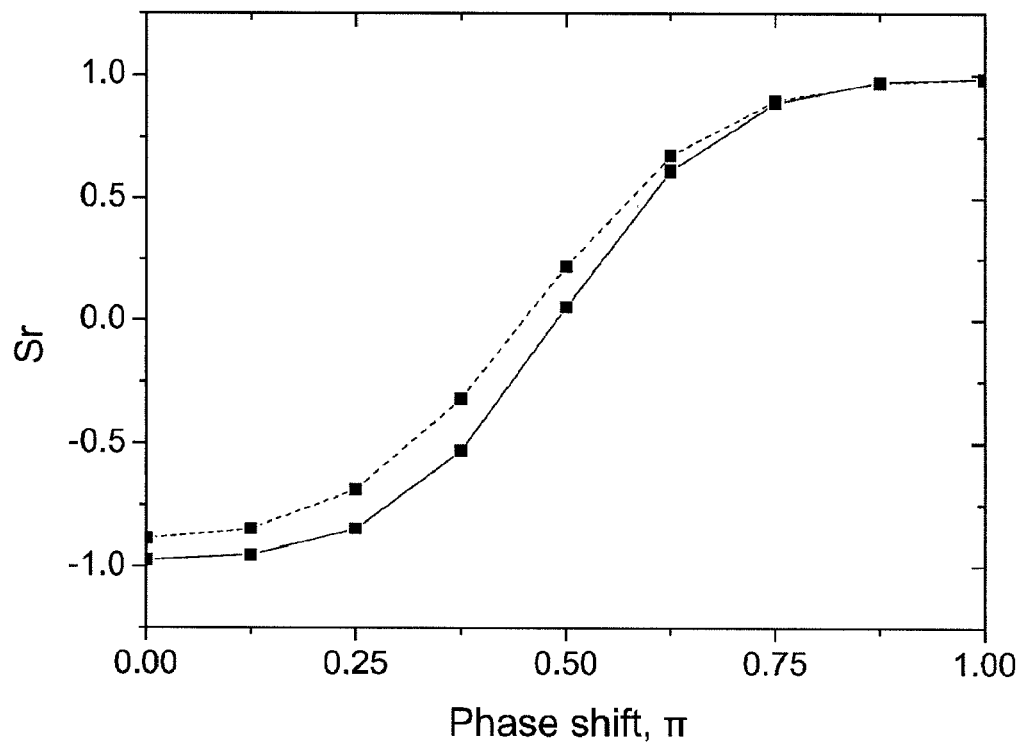
FIG. 8 shows two simulations of the signals detected at the output of an interferometer of the invention.

$U_{up}$, $U_{down}$ are the signals generated by the upper and the lower sections of the photodetector respectively. The results of the simulations ($S_r$ versus the phase shift) are presented in FIG. 8. All calculations were performed for a wavelength of 632.8 nm. The amplitudes of the modes were previously normalized to unity. The curve built for the 400 nm thick waveguide (solid line) is a little steeper than that for 300 nm thick waveguide (dash line). The reason is that the non-symmetrical distribution of the waveguide modes which is getting stronger for the thin waveguides. However, the difference between the curves slopes is not that remarkable: $4/\pi$ for the waveguide with thickness of 300 nm and $4.3/\pi$ for the 400 nm thick waveguide.

Considering a uniform bimodal waveguide with the modes propagating until reaching a distance L and the exit of the waveguide, the sensitivity of the device, i.e., the relationship between the change occurred in the output signal and the change occurred in the refractive index of the cladding layer, is expressed by the formula:

$$Sens = \frac{\partial Sr}{\partial n_{cl}} = \frac{\partial Sr}{\partial \varphi} \cdot \frac{\partial \varphi}{\partial n_{cl}} \quad (2)$$

$n_{cl}$ indicates the refractive index of the cladding layer, and $\varphi$ is the phase difference of both modes.

The phase difference due to a change in the refractive index of the cladding layer after a distance L is expressed as:

$$\Delta\varphi = \frac{2\pi}{\lambda} \cdot (\Delta n_{eff}^1 - \Delta n_{eff}^0) \cdot L \quad (3)$$

L is the length of the sensor plate, $\lambda$ is the wavelength, $\Delta n_{eff}^0$, $\Delta n_{eff}^1$ is the change of the effective refractive index of the zero and the first order modes respectively due to the changes in the refractive index of the cladding layer. After substitution of (3) with (2) the expression for the sensitivity of the device is obtained:

$$Sens = \frac{\partial Sr}{\partial \varphi}\left(\frac{\partial n_{eff}^1}{\partial n_{cl}} - \frac{\partial n_{eff}^0}{\partial n_{cl}}\right)\frac{2\pi}{\lambda} L \quad (4)$$

Figure 9:
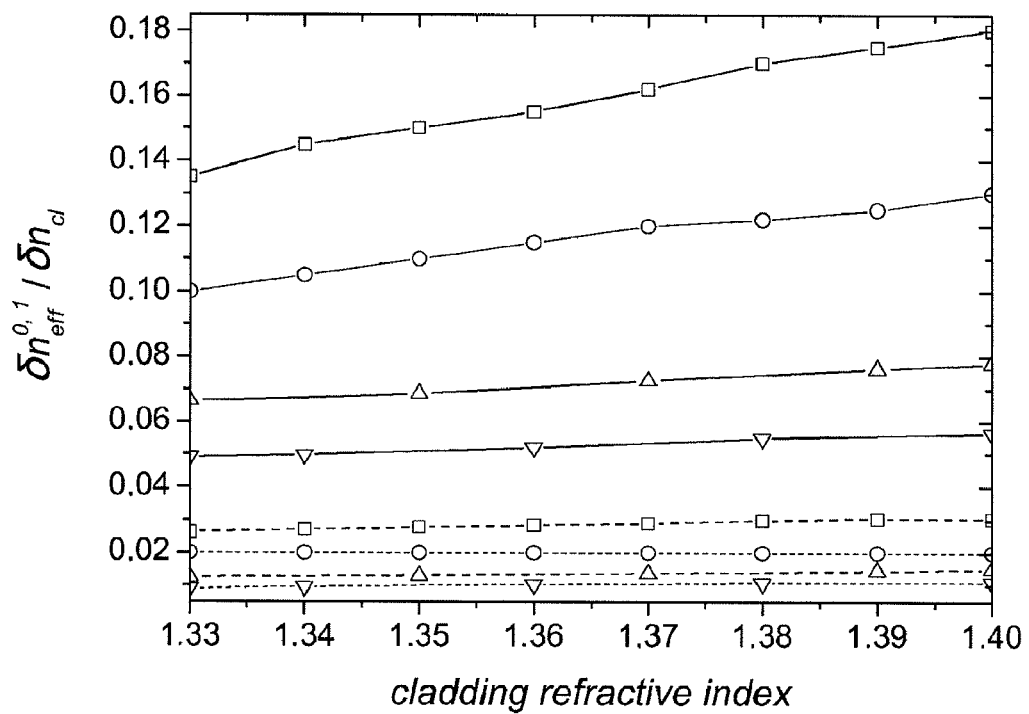
FIG. 9 shows a simulation which represents how the refractive index of the cladding layer affects the propagation constants of the two modes according to the invention.

The refractive index of the cladding layer differently affects the propagation constants $n_{eff}^0$ of the fundamental and $n_{eff}^1$ of the first order modes. The derivatives $$\frac{\partial n_{eff}^1}{\partial n_{cl}}, \frac{\partial n_{eff}^0}{\partial n_{cl}}$$

are presented in FIG. 9 as a function of the refractive index of the cladding layer. Dash lines correspond to the fundamental mode, solid lines correspond to the first mode. The waveguide thickness corresponds to: □—300 nm, ○—350 nm, △—420 nm, ▽—470 nm. Obviously, the deeper the waveguide modes penetrate into the cladding, the more effective refractive index modulation for both modes. The penetration of the modes is inversely proportional to the waveguide thickness and directly proportional to $n_{cl}$. The derivatives shown in FIG. 9 referred to both modes, increase as the refractive index of the cladding layer increases. However, the propagation constant of the first order mode is strongly affected by the cladding refractive index changes. The difference between the derivatives is especially significant, and subsequently the sensitivity is higher, in thin waveguides. For example, in a 300 nm thick waveguide, sensitivity can be three times higher than in a 470 nm thick waveguide.

The sensitivity expressed in terms of phase shift per unit of refractive index can be seen in FIG. 9 and expression (3). Thus, on a 300 nm thick and 10 mm long waveguide, a phase change of 2π can be reached, if the refractive index of the cladding layer changes by 6×10$^{-4}$ RIU (Refractive Index Unit), when n$_{cl}$ is around 1.34.

Figure 10:
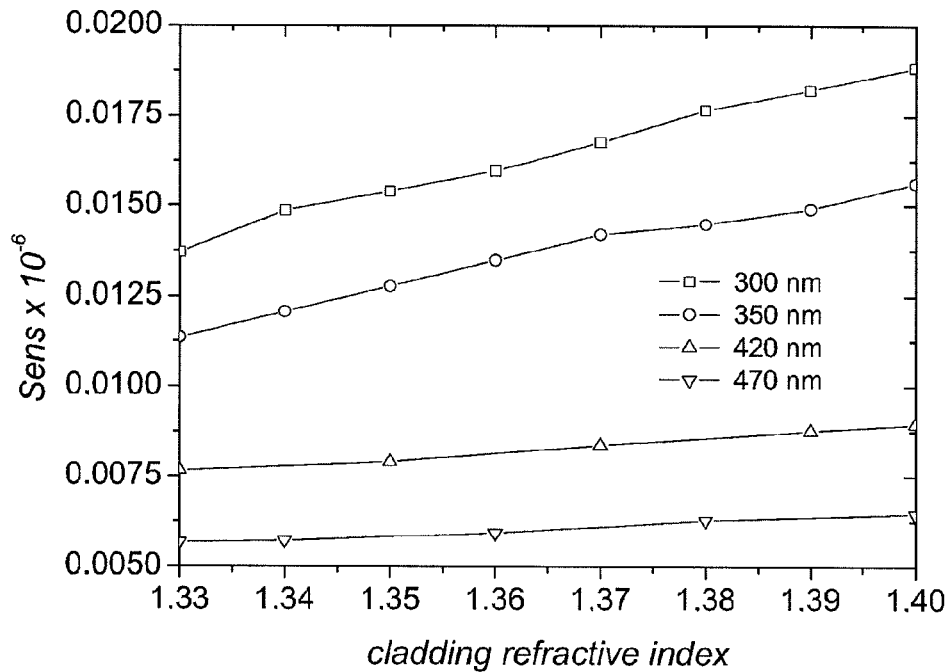
FIG. 10 represents the sensitivity versus the refractive index of the cladding layer according to the invention.

In FIG. 10 the sensitivity Sens calculated by means of expression (4) is plotted versus the refractive index of the cladding layer for four different waveguide thicknesses: □—300 nm, ○—350 nm, Δ—420 nm, ∇—470 nm. The sensitivity is the change in the output signal per unit refractive index change in the cladding layer. The calculations were performed assuming a 10 mm long waveguide. This parameter defines the noise floor which is allowed in the detection circuitry in order to distinguish the changes in the interference pattern. It can be observed that an accuracy of 1% is enough for the reading of the output signal when working with waveguides thinner than 400 nm. The sensitivity of the proposed device is comparable to the sensitivity of integrated MZI fabricated by silicon technologies.

The following is an example of preparation: A silicon wafer polished at one side is subjected to high temperature oxidation. A layer of silicon dioxide of about 2 μm thick is formed on both sides of the wafer (the side where components are placed, forming the waveguide, and the back side), as a result of this process. A layer of silicon nitride of about 400 nm thick is deposited by LPCVD technique on both the components and the back sides. A layer of PECVD silicon dioxide is deposited on the front side of the wafer. Waveguides are patterned on the front side using conventional photolithography and wet etching in buffered Hydro Fluoridric (HF) acid. Photoresist is removed with oxygen plasma. The wafer is immersed in HF solution for a time sufficient to remove the silicon dioxide mask and to form simultaneously ribs over the silicon nitride. Selective etching is used (the thickness of PECVD oxide is chosen proportional to the rib height). The selectivity of the etching (silicon nitride) is approximately 1000/14 if the etching is done with a SiO-etch solution (similar to HF10%). This technology allows manufacturing rib waveguides with a height of about 4 nm and width of about 4 μm. The resulting waveguide can support two transverse modes. It is therefore bimodal, having a fundamental mode and a first order mode. A layer of silicon oxide is then deposited on the part of the components as a protection layer. A sensor plate is formed on the surface of the waveguide by means of standard photolithography and wet etching in SiO-etch solution.

For the current experiment a 3 μm wide waveguide which supported a single mode in lateral direction was used. The wafer was diced in chips and the chips were polished to get the end faces of the waveguides polished. The chip was mounted on an aluminium base and covered with a polymethylmetacrylate (PMMA) microfluidic header which had a channel in order to provide the reagent flow over the waveguide. The length of the sensor plate L was 3 mm.

Figure 11:
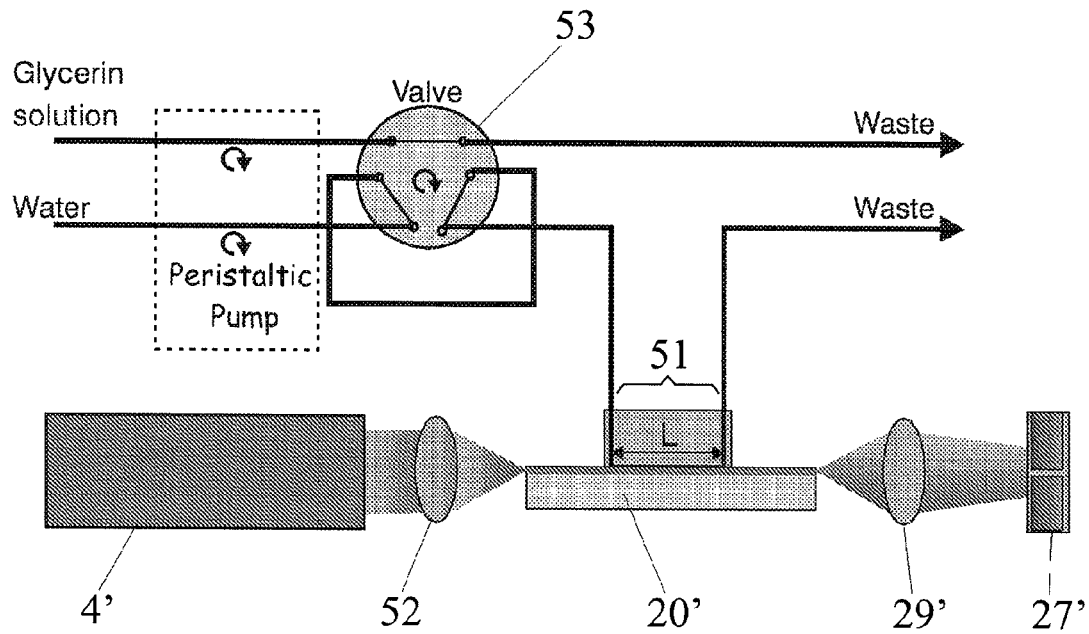
FIG. 11 shows a schematic view of an experimental set-up of a sensor according to the invention.
Figure 12A:
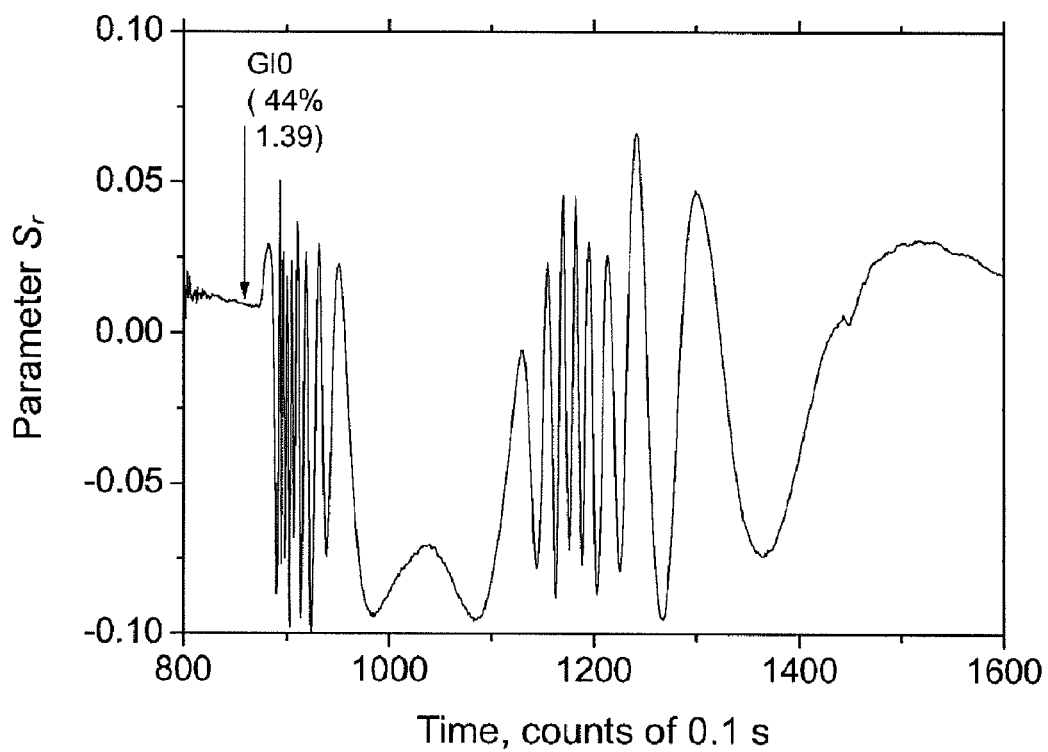
FIGS. 12a and 12b show the response of the sensor of FIG. 11 under different conditions.
Figure 12B:
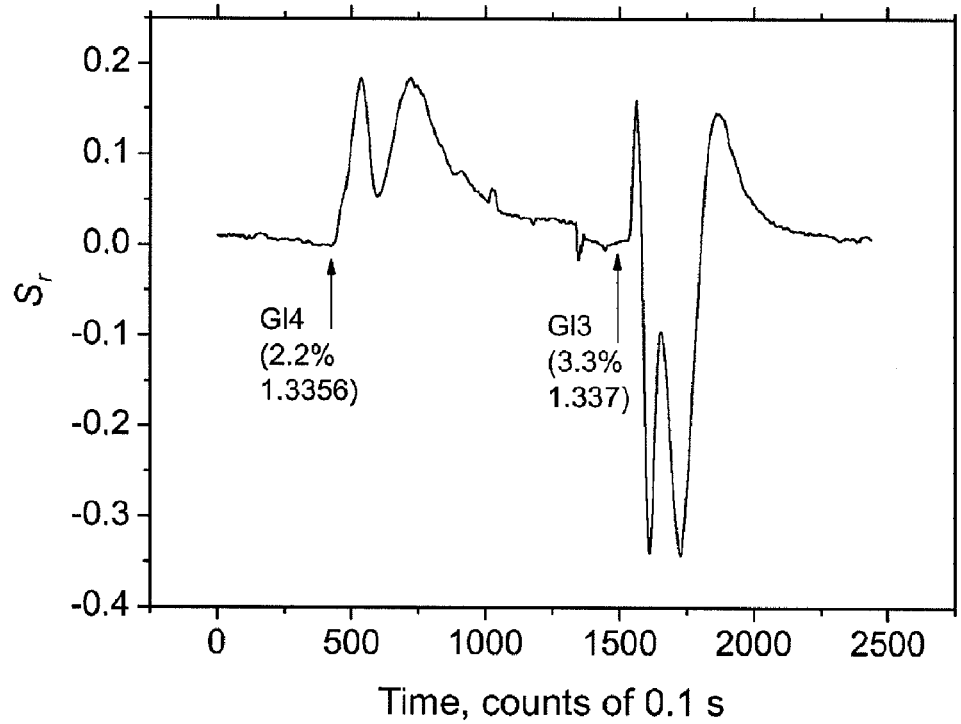

Next a biosensor based on a bimodal optical waveguide according to the invention is described. Experiments on the detection of the reagent refractive index changes were done by injecting water:glycerine solution into the channel. The schematic view of the experimental set-up is presented in FIG. 11. The flow was provided by a peristaltic pump. Light was launched into the waveguide 20' through an objective lens 52 focused to a beam from a He—Ne laser 4'. In this case, the laser is a HeNe Laser of 10 mW, which also comprises a beam expander. Slight misalignment of the objective with respect to the waveguide in vertical direction allows for excitation of both modes simultaneously. Light was collected by another objective lens 29' and the image of the waveguide facet was projected onto the TSP 27'. The signal was stabilized while deionized water was passing by the sensor plate 51. Valve 53 is used for directing the flow with or without reagent to a channel passing in the microfluidic cell by the sensor plate 51. Then solutions with three different concentrations, with indexes of refraction 1.3356, 1.337, and 1.39, were injected into the channel. In FIGS. 12a and 12b the time diagrams of the output signal are presented. The experiments were carried out on different samples and at different times, so the modulation amplitudes and sensitivities vary from one experiment to another. Injection of highly concentrated solution of glycerine (44% vol. and refractive index of 1.39) caused a strong phase change and 18π oscillations (see FIG. 12a). Injection of low concentrated solution of glycerine (2.2% or 3.3% vol. with corresponding refractive indexes of 1.3356 and 1.337, correspondingly) resulted in a weak phase changes and almost π and 2π oscillations, respectively (see FIG. 12b).

Analyzing the results of the experiments and assuming the refractive index of deionized water of 1.333, a phase change of about 2π per 0.006 cladding RIU change was observed. The curve slope at the most sensitive position is around 0.06 per 10$^{-4}$ RIU. Subsequently in order to detect index variation of 10$^{-6}$ RIU an accuracy of 6×10$^{-4}$ (0.06%) in measuring the absolute value of the output signal is required. Stability of the output signal must be of the same order of magnitude. Assuming the sensor plate to be 10 mm long, the sensitivity is 0.002 per 10$^{-6}$ RIU change. Although there are some discrepancies between the theoretically predicted sensitivities and the experimentally demonstrated ones, they are due to the coupling technique used in the experiment, which cannot always guaranty the appropriate amplitude ratio between the excited modes. In other words, this discrepancy is a consequence of engineering limitations.

The present invention further provides a method for detecting the introduction of changes (e.g., the amount or concentration of a stimulus) in a determined chemical, biological or physical stimulus in a localized environment. The method comprises the following steps carried out in a bimodal optical waveguide interferometer like the one shown in FIGS. 1a, 1b and 1c:

(a) defining a sensor plate 21 31 41 in a localized environment of the upper part of the waveguide 10 20 30 40;

(b) placing a chemical, biological or physical stimulus or analyte in said sensor plate 21 31 41;

(c) introducing or causing changes in said chemical, biological or physical stimulus in said sensor plate 21 31 41;

(d) coupling a fundamental mode and a first-order mode of electromagnetic radiation into said optical waveguide 10 20 30 40, in such a way that when both modes travel through the sensor plate 21 31 41 defined in the waveguide, they suffer a variation in its characteristics, such as a phase delay, which is dependent on the changes in said chemical, biological or physical stimulus;

(e) at the output of said waveguide, measuring the response of said fundamental mode relative to the response of said first-order mode; and (f) relating said relative response of both modes to the changes in the chemical, biological or physical stimulus.

Preferably, step (e) comprises:

(e1) generating a pattern of interference fringes; and (e2) measuring a displacement in the interference pattern.

Preferably, step (f) comprises:

(f1) relating the displacement in the interference pattern with the presence of changes in the determined chemical, biological or physical stimulus.

In conclusion, an interferometer and a biosensor based on a bimodal optical waveguide having a simple design are presented.

In this text, the term "comprises" and its derivations (such as "comprising", etc.) should not be understood in an excluding sense, i.e., these terms should not be interpreted as excluding the possibility that what is described and defined may include further elements, steps, etc.

In the context of the present invention, the terms "around", "about", "approximately" and "substantially" and terms of the same family (such as "approximate", etc.) should be understood as indicating values very near to those which accompany the aforementioned term. That is to say, a deviation within reasonable limits from an exact value should be accepted, because the expert in the technique will understand that such a deviation from the values indicated is inevitable due to measurement inaccuracies, etc.

On the other hand, the invention is obviously not limited to the specific embodiment(s) described herein, but also encompasses any variations that may be considered by any person skilled in the art (for example, as regards the choice of materials, dimensions, components, configuration, etc.), within the general scope of the invention as defined in the appended claims.

What is claimed is:

1. Planar optical waveguide interferometer (15, 25, 35, 45) comprising:
   a substrate (8, 28, 38, 48);
   a bimodal waveguide (10, 20, 20', 30, 40) comprising at least one layer (1, 2, 3) deposited on said substrate (8, 28, 38, 48), said bimodal waveguide (10, 20, 20', 30, 40) being designed for supporting a zero-order and a first-order transverse propagating modes, said transverse propagating modes having different dispersion;
   a sensor plate (21, 31, 41, 51) located in a specific area of the upper side of said bimodal waveguide (10, 20, 20', 30, 40), said sensor plate (21, 31, 41, 51) being configured for receiving a chemical, biological or physical input stimulus, said stimulus being capable of changing the effective refractive index of said bimodal waveguide (10, 20, 20',30, 40);
   characterized in that
   said bimodal waveguide (10, 20, 20', 30, 40) further comprises confining means (9) designed for confining light in lateral direction, the bimodal waveguide (10, 20, 20', 30, 40) being thus designed for supporting one lateral mode.

2. Planar optical waveguide interferometer (15, 25, 35, 45) according to claim 1, comprising an electromagnetic radiation source (4, 4') configured for leading optical light into said bimodal waveguide (10, 20, 20', 30, 40).

3. Planar optical waveguide interferometer (15, 25, 35, 45) according to claim 2, wherein said electromagnetic radiation source (4, 4') is a laser.

4. Planar optical waveguide interferometer (15, 25, 35, 45) according to claim 2, wherein said electromagnetic radiation source is integrated within the structure of the substrate (8, 28, 38, 48).

5. Planar optical waveguide interferometer (15, 25, 35, 45) according to claim 1, comprising polarizing means.

6. Planar optical waveguide interferometer (15, 25, 35, 45) according to claim 1, further comprising other focusing means.

7. Planar optical waveguide interferometer (15, 25) according to claim 6, wherein said focusing means is a lens (22, 52).

8. Planar optical waveguide interferometer (15, 25) according to claim 7, wherein the central axis of said lens (22, 52) is configured to be misaligned in the transverse direction with respect to the longitudinal symmetry axis of the bimodal waveguide (20, 20'), thereby a first and a second transverse propagating modes being excited within the bimodal waveguide (20), 20' when light from a source is directly focused through said lens towards the bimodal waveguide (20, 20').

9. Planar optical waveguide interferometer (35) according to claim 1, comprising:
   an input waveguide (32) connected at one end of said bimodal waveguide (30), said input waveguide (32) being designed for supporting a single mode in both transverse and lateral directions;
   an output waveguide (33) connected at the other end of said bimodal waveguide (30), said output waveguide (33) being designed for supporting a single mode in both transverse and lateral directions;
   wherein the thickness of each of said input and output waveguides (32, 33) is less than that of said bimodal waveguide (30), such that due to the non-symmetrical geometry of the structure at the junction of said input waveguide (32) and said bimodal waveguide (30), said single mode is split into said first and second transverse propagating modes.

10. Planar optical waveguide interferometer (35) according to claim 9, further comprising means for coupling electromagnetic radiation into said bimodal waveguide (30), wherein said means are selected from the group formed by: end-fire, direct focusing, prism coupling and diffraction grating coupling.

11. Planar optical waveguide interferometer (35) according to claim 9, wherein the amount of light coupled into the output waveguide (33) depends on the intensity distribution existing at the junction between the bimodal waveguide (30) and the output waveguide (33).

12. Planar optical waveguide interferometer (45) according to claim 1, comprising coupling means (42) designed for coupling to said bimodal waveguide (40) a first and a second order modes of light with different incidence angles ($\theta_0$, $\theta_1$).

13. Planar optical waveguide interferometer (45) according to claim 12, wherein said coupling means (42) is a diffraction grating coupled to an input of said bimodal waveguide (40).

14. Planar optical waveguide interferometer (15, 25, 35, 45) according to claim 1, wherein said bimodal waveguide (10, 20, 20', 30, 40) comprises at least two layers.

15. Planar optical waveguide interferometer (15, 25, 35, 45) according to claim 14, wherein a first waveguide layer has a first refractive index and a second waveguide layer has a second refractive index, the refractive index of said second layer being lower than that of said first waveguide layer.

16. Planar optical waveguide interferometer (15, 25, 35, 45) according to claim 1, wherein the effective refractive index of said zero-order mode and the effective refractive index of said first-order mode are substantially different.

17. Planar optical waveguide interferometer (15, 25, 35, 45) according to claim 1, wherein said different dispersion of said transverse propagating modes depends on the propagation velocity on the parameters of said waveguide.

18. Planar optical waveguide interferometer (15, 25, 35, 45) according to claim 1, further comprising detection means (27, 27', 37, 47) for measuring at the output of said waveguide changes in the radiation intensity due to said input stimulus.

19. Planar optical waveguide interferometer (15, 25, 35, 45) according to claim 18, wherein said detection means (27, 27', 37, 47) is a two-section photodetector.

20. Chip comprising at least one planar optical waveguide interferometer (15, 25, 35, 45) according to claim 1.

21. Sensor comprising a planar optical waveguide interferometer (15, 25, 35, 45) according to claim 1.

22. Sensing method comprising the following steps:
(a) defining a sensor plate (21, 31, 41, 51) in a specific area of a bimodal waveguide (10, 20, 20', 30, 40) of an optical waveguide interferometer (15, 25, 35, 45);
(b) placing a chemical, biological or physical stimulus in said sensor plate (21, 31, 41, 51);
(c) introducing or causing changes in said chemical, biological or physical stimulus placed in said sensor plate (21, 31, 41, 51);
(d) coupling a zero-order mode and another first-order mode of electromagnetic radiation into said bimodal waveguide (10, 20, 20', 30, 40), in such a way that when both modes travel through the sensor plate (21, 31, 41, 51) defined in the bimodal waveguide (10, 20, 20', 30, 40), they suffer a phase delay which is dependent on the changes in said chemical, biological or physical stimulus;
(e) at the output of said bimodal waveguide (10, 20, 20', 30, 40), measuring the response of said zero-order mode relative to the response of said first-order mode; and
(f) relating said relative response of both modes to the changes in the chemical, biological or physical stimulus.

23. Sensing method according to claim 22, wherein the step of measuring the response of said zero-order mode relative to the response of said first-order mode comprises:
generating a pattern of interference fringes (11, 12, 13); and
measuring a displacement in the interference pattern (11, 12, 13).

24. Sensing method according to claim 23, wherein the step of relating said relative response of both modes to the changes in the chemical, biological or physical stimulus comprises:
relating said displacement in the interference pattern to the presence of changes in the determined chemical, biological or physical stimulus.

* * * * *